US007922660B2

(12) United States Patent
Sonek et al.

(10) Patent No.: US 7,922,660 B2
(45) Date of Patent: Apr. 12, 2011

(54) METHODS OF PRENATAL SCREENING FOR TRISOMY 21

(76) Inventors: Jiri D. Sonek, Beavercreek, OH (US); Kypros H. Nicolaides, London (GB)

(*) Notice: Subject to any disclaimer, the term of this patent is extended or adjusted under 35 U.S.C. 154(b) by 923 days.

(21) Appl. No.: 11/888,554

(22) Filed: Aug. 1, 2007

(65) Prior Publication Data

US 2008/0188748 A1 Aug. 7, 2008

Related U.S. Application Data

(60) Provisional application No. 60/834,579, filed on Aug. 1, 2006, provisional application No. 60/872,880, filed on Dec. 5, 2006.

(51) Int. Cl.
*A61B 8/00* (2006.01)
(52) U.S. Cl. .......................... 600/437; 382/128
(58) Field of Classification Search .................. 600/437, 600/438, 443; 302/128, 181, 190, 201–203, 302/286
See application file for complete search history.

(56) References Cited

OTHER PUBLICATIONS

Rotten et al. The fetal mandible: a 2D and 3D sonographic approach to the diagnosis of retrognathia and micrognathia. Ultrasound in Obstetrics and Gynecology. vol. 19(2):122-130. 2002.*
Sonek et al, "Frontomaxillary facial angles in screening for trisomy 21 at 14-13 weeks' gestation", American Journal of Obstetrics & Gynecology, Aug. 2007, 160.e1-160.e5.
Cicero et al, "Absence of nasal bone in fetuses with trisomy 21 at 11-14 weeks of gestation: an observational study", The Lancet, vol. 358, Nov. 17, 2001, pp. 1665-1667.
Sonek et al, "Nasal bone assessment in prenatal screening for trisomy 21", American Journal of Obstetrics & Gynecology, (2006), 195, pp. 1219-1230.
Sonek et al, "Prenatal ultrasonographic diagnosis of nasal bone abnormalities in three fetuses with Down syndrome", American Journal of Obstetrics & Gynecology, Jan. 2002, 186: pp. 139-141.
Sonek et al, "Frontomaxillary facial angle in fetuses with trisomy 21 at 11-13 weeks", American Journal of Obstetrics & Gynecology, Mar. 2007, 196: pp. 271.e1-271.e4.
Cicero et al, "Maxillary length at 11-14 weeks of gestation in fetuses with trisomy 21", Ultrasound Obstet. Gynecol, 2004; 24: pp. 19-22.
Allanson, J.E., et al. "Anthropometric Craniofacial Pattern Profiles in Down Syndrome," American Journal of Medical Genetics 47:748-752 (1993).
Sonek, Jiri, et al., "Frontomaxillary Facial Angle In Fetuses With Trisomy 21 at 11-13/6 Weeks," American Journal of Obstetrics & Gynecology, Mar. 2007, 271.e1-271.e4.
Mestrovic, S. Rajic, et al., "Hypodontia In Patients With Down's Syndrome", Coll. Antropol. 22 (Suppl.) (1998) 69-72.
Shapira, Joseph, et al. "Prevalence of Tooth Transposition, Third Molar Agenesis, and Maxillary Canine Impaction in Individuals with Down Syndrome," Angle Orthodontist, vol. 70, No. 4, 2000, 290-296.

(Continued)

*Primary Examiner* — Brian Casler
*Assistant Examiner* — Parikha S Mehta
(74) *Attorney, Agent, or Firm* — Dinsmore & Shohl

(57) ABSTRACT

Methods for prenatal screening for trisomy 21 employ examination of the fronto-maxillary facial (FMF) angle of a fetus. The methods may comprise obtaining a two or three dimensional image of a fetal face, measuring the $FMF_{bone}$ angle and/or $FMF_{skin}$ angle on the image, and comparing the measured $FMF_{bone}$ angle and/or $FMF_{skin}$ angle with an $FMF_{bone}$ angle and/or $FMF_{skin}$ angle characteristic of chromosomally normal fetuses. A measured $FMF_{bone}$ angle and/or $FMF_{skin}$ angle greater than the $FMF_{bone}$ angle and/or $FMF_{skin}$ angle characteristic of chromosomally normal fetuses provides an indication of an increased likelihood of the occurrence of trisomy 21 in the fetus.

19 Claims, 6 Drawing Sheets

OTHER PUBLICATIONS

Bergann, Anna, et al., "Mid-Facial Anthropometry In Second-Trimester Fetuses With Trisomy 21: A Three-Dimensional Ultrasound Study," Prenatal Diagnosis; Prenat Diagn 2006: 158-162.

Kumasaka, Satsuki, et al., "Oligodontia: A Radiographic Comparison of Subjects With Down Syndrome and Normal Subjects," SCD Special Care in Dentistry, vol. 17 No. 4 1997, 137-141.

Bland, J. Martin, et al., "Statistical Methods for Assessing Agreement Between Two Methods of Clinical Measurement," The Lancet, February 8, 1986, 307-310.

Farkas, Leslie G. et al., "Surface Anatomy of the Face in Down's Syndrome: Linear and Angular Measurements in the Craniofacial Regions," The Journal of Craniofacial Surgery, Jul. 2001; 12(4): 373-380.

Dagklis, T., et al., "Three-Dimensional Evaluation of Mid-Facial Hypoplasia in Fetuses with Trisomy 21 At 11 + 0 to 13 + 6 Weeks of Gestation," Ultrasound Obstet. Gynecol. 2006: 28: 261-265.

Russell, Bjorn G., et al., "Tooth Agenesis in Down Syndrome," American Journal of Medical Genetics, Feb. 13, 1995; 55 (4): 466-71.

Sonek et al, "Prenatal ultrasonographic diagnosis of nasal bone abnormalities in three fetuses with Down Syndrome," American Journal of Obstetrics & Gynecology, Jan. 2001, 186:139-141.

Sonek et al, "Nasal bone assessement in prenatal screening for trisomy 21," American Journal of Obstetrics & Gynecology (2006), 195:1219-1230.

Cicero et al, "Maxillary length at 11-14 weeks of gestation in fetuses with trisomy 21," Ultrasound Obstet. Gynecol. 2004, 24:19-22.

* cited by examiner

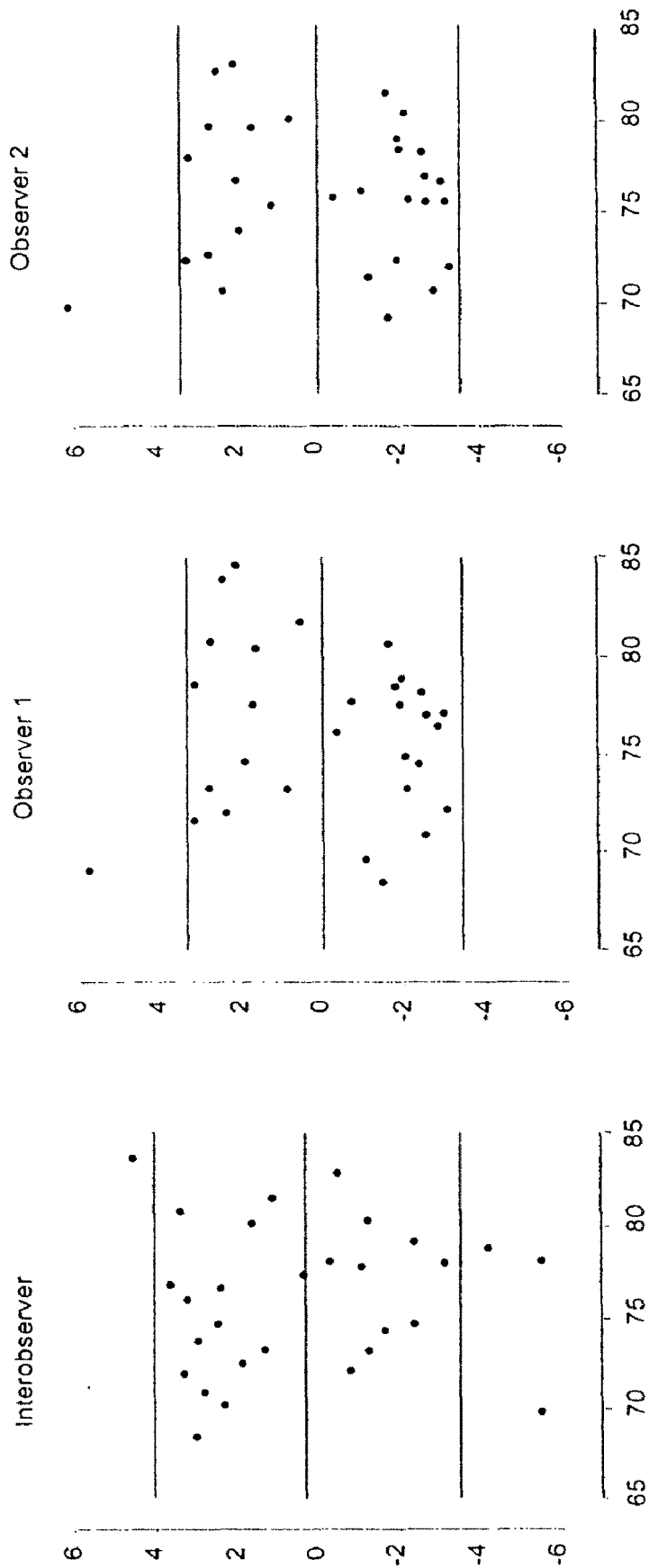

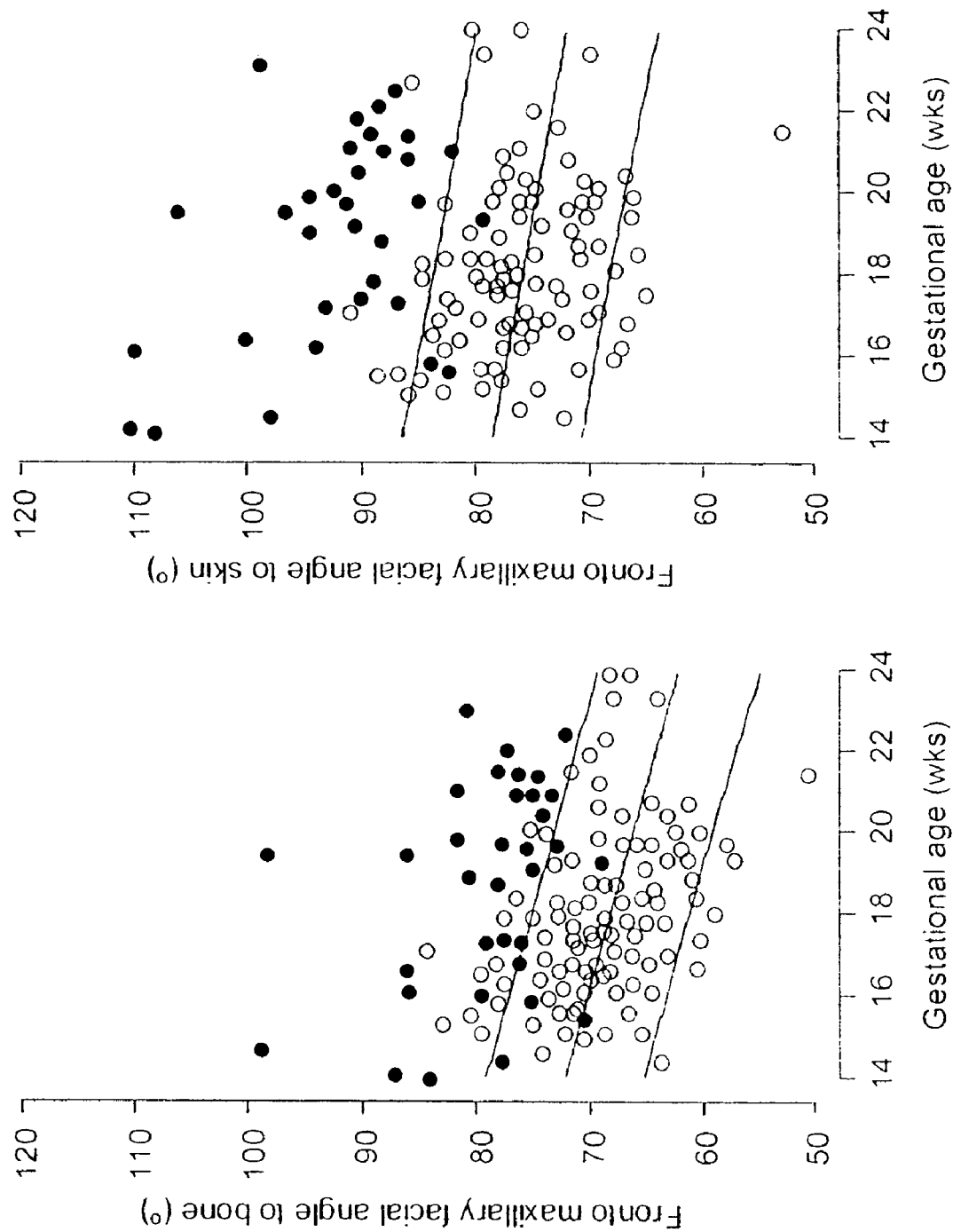

METHODS OF PRENATAL SCREENING FOR TRISOMY 21

CROSS-REFERENCES TO RELATED APPLICATIONS

The present application claims the benefit under 35 U.S.C. §119 of U.S. Application Ser. Nos. 60/834,579 filed Aug. 1, 2006 and 60/872,880 filed Dec. 5, 2006, both of which are incorporated herein by reference.

FIELD OF THE INVENTION

The present invention is directed to methods for prenatal screening for trisomy 21, the most common form of Down syndrome, by examination of the fronto-maxillary facial (FMF) angle of a fetus.

BACKGROUND OF THE INVENTION

Down syndrome is a genetic condition in which a person has 47 chromosomes instead of the usual 46. In most cases, Down syndrome occurs when there is an extra copy of chromosome 21. This form of Down syndrome is known as trisomy 21.

Trisomy 21 is associated with a specific phenotype, which includes a flat profile. This observation is part of Langdon Down's original description of what later became known as Down syndrome. Several radiological studies have reported underdevelopment of the upper jaw, delayed dental growth, reduction in the number and size of teeth, and absence or hypoplasia of the nasal bone in individuals with trisomy 21. See, for example, Farkas et al, "Surface anatomy of the face in Down's syndrome: linear and angular measurements in the craniofacial regions," *J Craniofac Surg*, 12:373-9 (2001); Allanson et al, "Anthropometric craniofacial pattern profiles in Down syndrome," *Am J Med Genet*, 47:748-52 (1993); impaction in individuals with Down syndrome," *Orthod*, 70:290-6 (2000); Mestrovic et al, "Hypodontia in patients with Down's syndrome," *Coll Antropol*, 22:69-72 (1998); Kumasaka et al, "Oligodontia: a radiographic comparison of subjects with Down syndrome and normal subjects," *Spec Care Dentist*, 17:137-41 (1997); and Russell et al, "Tooth agenesis in Down syndrome," *Am J Med Genet*, 55:466-71 (1995).

Furthermore, prenatal sonographic studies have reported that a significant proportion of fetuses with trisomy 21 have shortening of the maxillary length and maxillary depth. See, for example, Cicero et al, "Maxillary length at 11-14 weeks of gestation in fetuses with trisomy 21," *Ultrasound Obstet Gynecol*, 24:19-22 (2004); Dagklis et al, "Three-dimensional evaluation of mid-facial hypoplasia in fetuses with trisomy 21 at 11-13+6 weeks," *Ultrasound Obstet Gynecol*, 28(3): 261-5 (September 2006); and Berganni et al, "Mid-facial anthropometry in second-trimester fetuses with trisomy 21: a three dimensional ultrasound study," *Prenatal Diagnosis*, 26:158-162 (2006). However, from these studies, the reported differences between maxillary measurements between trisomy 21 and euploid fetuses have not been shown to be large enough to be clinically useful. For example, Cicero et al describe a 2D sonographic study at 11-13$^{+6}$ weeks which showed that trisomy 21 fetuses had a significantly shorter maxillary length as compared to normal. It is below the 5th percentile of the normal range in 24% of affected fetuses. However, the degree of deviation from normal is too small (mean of 0.7 mm) for this measurement to be useful in screening for trisomy 21. Similarly, Dagklis et al describe a 3D sonographic study at 11-13$^{+6}$ weeks showing that in trisomy 21 fetuses the maxillary depth is shorter than normal by a mean of only 0.3 mm and it is below the 5th percentile of the normal range in only 10% of affected fetuses.

SUMMARY OF THE INVENTION

The present invention is directed to methods for prenatal screening for trisomy 21 by examination of the fronto-maxillary facial (FMF) angle of a fetus.

In one embodiment, the present invention is directed to a method for prenatal screening for trisomy 21, comprising obtaining a two or three dimensional image of a fetal face, measuring the angle between a line extending along the upper aspect of the maxilla and a line extending from the anterior aspect of the maxilla to the external surface of the frontal bone at the point of its greatest anterior excursion (the $FMF_{bone}$ angle) on the image, and comparing the measured $FMF_{bone}$ angle with an $FMF_{bone}$ angle characteristic of chromosomally normal fetuses, wherein a measured $FMF_{bone}$ angle greater than the $FMF_{bone}$ angle characteristic of chromosomally normal fetuses provides an indication of an increased likelihood of the occurrence of trisomy 21 in the fetus.

In another embodiment, the present invention is directed to a method for prenatal screening for trisomy 21 in a fetus at 14-23 weeks of gestation, comprising obtaining a two or three dimensional image of a fetal face, measuring the angle between a line extending along the upper aspect of the maxilla and a line extending from the anterior aspect of the maxilla to the external skin surface along the frontal bone at the point of its greatest anterior excursion (the $FMF_{skin}$ angle) on the image, and comparing the measured $FMF_{skin}$ angle with an $FMF_{skin}$ angle characteristic of chromosomally normal fetuses, wherein a measured $FMF_{skin}$ angle greater than the $FMF_{skin}$ angle characteristic of chromosomally normal fetuses provides an indication of a likelihood of the occurrence of trisomy 21 in the fetus.

These and additional embodiments of the present invention, and advantages thereof, will be more fully apparent and understood in view of the following detailed description.

BRIEF DESCRIPTION OF THE DRAWINGS

The following detailed description will be more fully understood in view of the drawing in which:

FIG. 3A shows inter observer agreement (Bland-Altman) expressed as difference in percentage against the mean of paired measurements for the facial angle ($FMF_{bone}$), while FIGS. 3B and 3C show individual observer values.

FIGS. 4A and 4B are ultrasound pictures of the fetal profile demonstrating the landmarks for the measurement of the fronto-maxillary facial (FMF) angles wherein FIG. 4A shows the upper line of the upper palate is marked by the interrupted line (a), the front part of the boney forehead by arrow (b) and the external surface of the skin over the lower part of the forehead just before the skin begins its anterior course over the nasal bridge by arrow (c), and FIG. 4B illustrates a hyperchoic line coursing diagonally through the upper palate which should not be mistaken as the upper border of the palate (arrows);

FIGS. 6A and 6B show the fronto-maxillary facial (FMF) angles in fetuses with trisomy 12 (•) and in euploid fetuses (○) plotted on the reference range with gestation (mean, 5th and 95th percentiles) for $FMF_{bone}$ and $FMF_{skin}$, respectively.

Figure 1B:
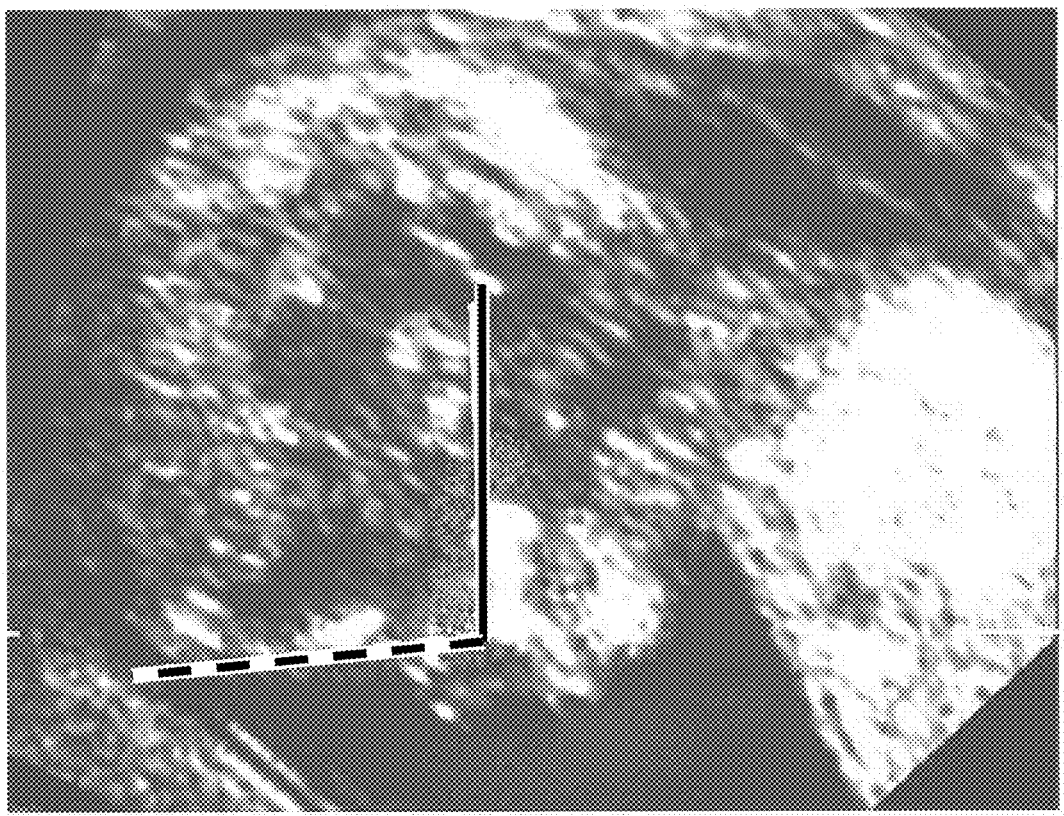
FIGS. 1A and 1B are ultrasound pictures comparing, respectively, the facial angle ($FMF_{bone}$) in a chromosomally normal fetus and one with trisomy 21.

The embodiments set forth in the drawing are illustrative in nature and are not intended to be limiting of the invention defined by the claims. Moreover, individual features of the drawing and the invention will be more fully apparent and understood in view of the detailed description.

DETAILED DESCRIPTION

The present invention is directed to methods for prenatal screening for trisomy 21 by examination of the fronto-maxillary facial (FMF) angle of a fetus. Particularly, from a two or three dimensional image of a fetal face, the angle between a line extending along the upper aspect of the maxilla, optionally along the vomer bone, and a line extending from the anterior aspect of the maxilla to the external surface of the frontal bone at the point of its greatest anterior excursion (the $FMF_{bone}$ angle) is employed, and/or the angle between a line extending along the upper aspect of the maxilla, optionally along the vomer bone, and a line extending from the anterior aspect of the maxilla to the external skin surface along the frontal bone at the point of its greatest anterior excursion (the $FMF_{skin}$ angle) is employed. One skilled in the art will recognize that a line extending along the maxilla and the vomer bone follows the upper palate.

The maxilla is the major bone of the upper jaw. The vomer bone is a single relatively flat bone located in the mid-sagittal plane. The frontal bone resembles a cockle-shell in form, and consists of two portions—a vertical portion, the squama, corresponding with the region of the forehead; and an orbital or horizontal portion, which enters into the formation of the roofs of the orbital and nasal cavities. The forehead portion of the frontal bone is employed herein.

In a specific embodiment, the image of the fetal face is obtained through three dimensional ultrasound, although other imaging techniques may be employed if desired. In a further embodiment, the image comprises a mid-sagittal view of the fetal face obtained through three dimensional ultrasound. According to techniques known in the art, the three dimensional fetal face volumes may be displayed in the three orthogonal planes that compose the multiplanar mode of the three dimensional image. In this mode, an optimal sagittal view is produced to show the fetal profile. As this plane is scrolled, a series of corresponding transverse and coronal images of the fetal face are simultaneously demonstrated. A mid-sagittal view of the fetal face showing the maxilla is thus obtained. The fronto-maxillary facial (FMF) angles as defined are measured from the resulting images.

The methods of the present invention may be performed at anytime beginning at about 10 weeks of gestation. Thus, in one embodiment, the image is obtained from a fetus at 10 or greater weeks of gestation. In another embodiment, the image is obtained from a fetus at 10-19 weeks of gestation. In yet a further embodiment, the image is obtained from a fetus at 11-13$^{+6}$ weeks of gestation. In another embodiment, the image is obtained from a fetus at 14-23 weeks of gestation. In another embodiment, the method of measuring and comparing the $FMF_{bone}$ angle is employed during the first trimester, for example, during weeks 10-13 of gestation, and the method of measuring and comparing the $FMF_{skin}$ angle is employed during the second trimester, for example, during weeks 14-23 of gestation.

As will be demonstrated below with respect to the examples, in one embodiment, a measured $FMF_{bone}$ angle of greater than about 85°, more specifically greater than about 90°, may provide an indication of an increased likelihood of the occurrence of trisomy 21 in the fetus. In another embodiment, a measured $FMF_{skin}$ angle of greater than about 80°, more specifically greater than about 85°, may provide an indication of an increased likelihood of the occurrence of trisomy 21 in the fetus.

The present methods are intended to be used in connection with other methods and procedures known in the prenatal art for assessing the likelihood of a trisomy 21 fetus. Such methods include, but are not limited to, review of maternal age and nuchal translucency measurement.

Langdon Down had made a number of critical observations in his initial description of the syndrome that later came to bear his name. Two of these have already been found to be useful in prenatal screening for trisomy 21. The first observation, that the skin is deficient in elasticity giving the appearance of being too large for the body, is presumably the basis of the prenatal finding of increased nuchal translucency in the first trimester and increased nuchal fold thickness in the second. The second observation of Langdon Down, that the face is flat and broad, and destitute of prominence, may be due to nasal hypoplasia, which has been described in affected fetuses during both the first and second trimesters of pregnancy. Another cause of the flat face is hypoplasia or dorsal displacement of the maxilla. Sonographic studies have reported that although in fetuses with trisomy 21, the maxilla is shorter, the difference in measurements between affected and euploid fetuses is not large enough to be clinically useful. In contrast, the FMF angle which provides an objective assessment of the dorsal displacement of the maxilla with respect to the forehead, is substantially higher in trisomy 21 fetuses than in euploid fetuses.

The following examples describe studies illustrating the procedures and advantages of the present methods.

Example 1

This retrospective study utilized 3D volumes of the fetal face, which are acquired before fetal karyotyping by chorionic villus sampling (CVS) at 11-13$^{+6}$ weeks of gestation. The fetuses are determined as being at risk of trisomy 21 based on the combination of maternal age and nuchal translucency measurement. Singleton pregnancies only are used. In each fetus, the crown-rump length and nuchal translucency thickness are measured in a standard fashion. A mid sagittal image of the fetal face is examined for the presence or absence of the nasal bone.

A database of stored images and diagnoses is reviewed and 100 consecutive cases of fetal trisomy 21 and 300 chromosomally normal fetuses in which a 3D volume of the fetal face had been obtained, are identified. The images are obtained with the fetus in the mid-sagittal plane with the transducer being parallel to the long axis of the nose. All 3D examinations are carried out transabdominally (RAB 4-8L probe, Voluson 730 Expert, GE Medical Systems, Milwaukee, Wis., USA), by sonographers with extensive experience in scanning and 3D ultrasound.

Figure 1A:
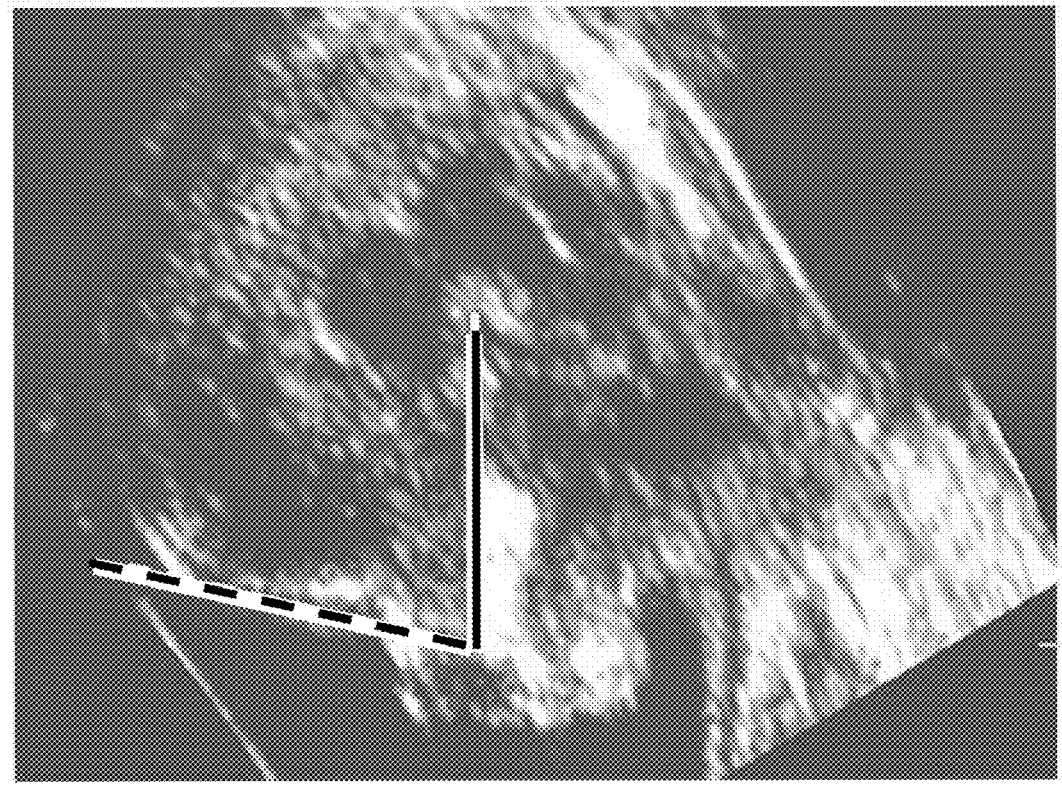

Analysis of the 3D volumes is carried out by sonographers who are not aware of the fetal karyotype. The 3D volumes are displayed in the three orthogonal planes that compose the multiplanar mode of the 3D image. In this mode, an optimal sagittal view is produced to show the fetal profile. As this plane is scrolled, a series of corresponding transverse and coronal images of the fetal face are simultaneously demonstrated. A mid-sagittal view of the fetal face showing the maxilla is thus obtained. The fronto-maxillary facial ($FMF_{bone}$) angle is measured. This angle is defined as the angle between a line extending along the upper aspect of the maxilla and a line extending from the anterior aspect of the maxilla to the external surface of the frontal bone at the point of its greatest anterior excursion as shown in FIGS. 1A (chromosomally normal fetus) and 1B (trisomy 21 fetus).

Statistical analysis: The potential association between the FMF angle and the crown-rump length, nuchal translucency thickness, presence or absence of nasal hypoplasia and fetal karyotype is examined using linear regression analysis. T-test for independent samples is used for the comparison of the FMF angle between chromosomally normal and trisomy 21 fetuses. The intra- and inter-observer agreement for the measurement of the FMF angle are tested in sets of 30 cases each, as described by Bland et al, "Statistical methods for assessing agreement between two methods of clinical measurement," *Lancet*, 1:307-10 (1986). The data are analyzed using the statistical software SPSS 13.0 (Chicago, Ill., USA) and Excel for Windows 2000 (Microsoft Corp., Redmond, Wash., USA). A p value of less than 0.05 is considered statistically significant.

Results: The median maternal age is 36 years of age (range 17 to 47) in both the trisomy 21 and the chromosomally normal groups. The median fetal crown-rump length is 68 (45-84) mm and the median gestation is 12 (11-13$^{+6}$) weeks in both groups. An absent nasal bone is found in 6 (2%) of the 300 chromosomally normal fetuses and in 58% of the 100 trisomy 21 fetuses. The $FMF_{bone}$ angle is successfully measured in all 400 cases.

Figures 2A, 2B:
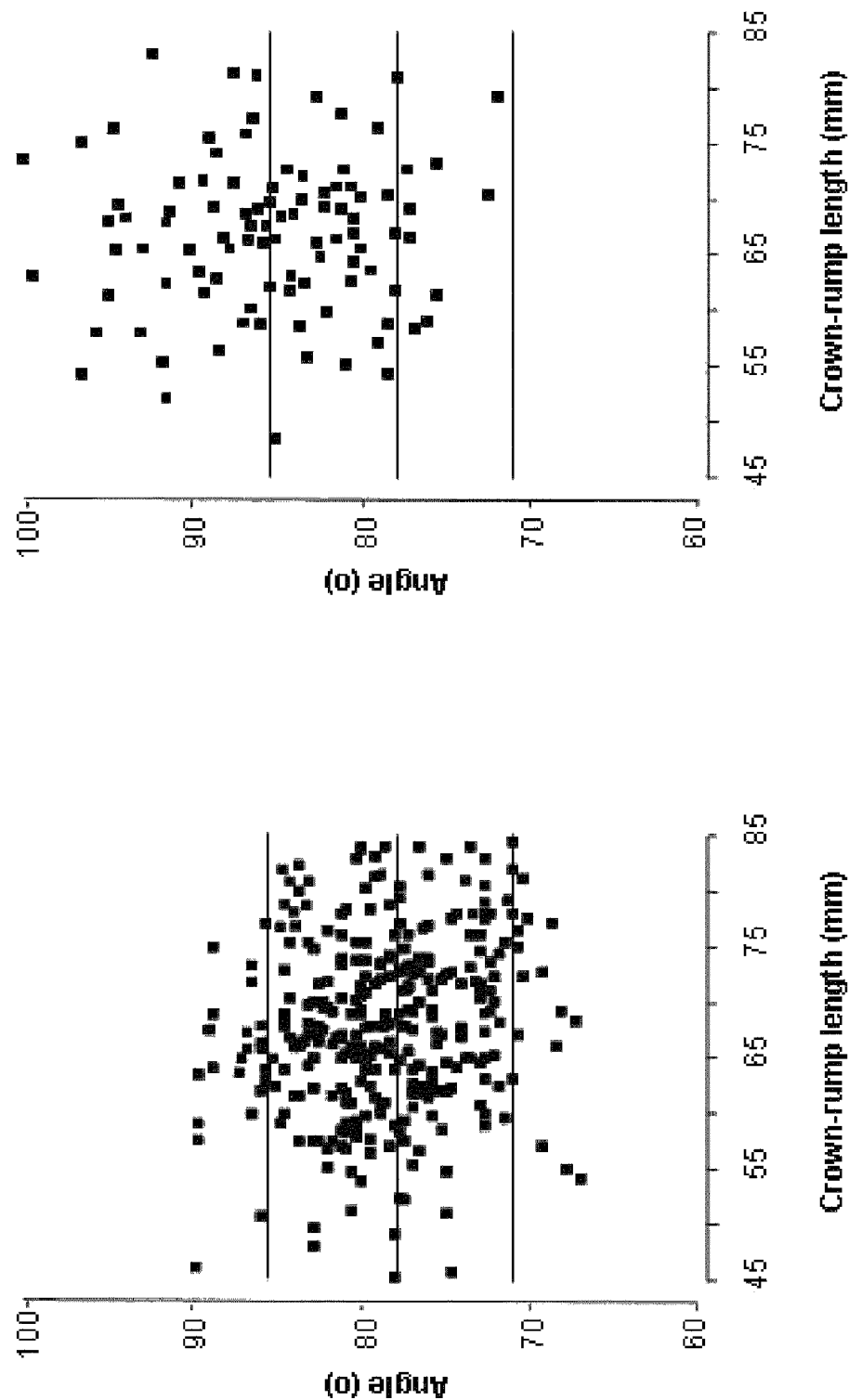
FIGS. 2A and 2B show facial angle ($FMF_{bone}$) in, respectively, chromosomally normal fetuses and trisomy 21 fetuses, plotted on the reference range (mean, 95th and 5th percentiles) with crown-rump length.

In the chromosomally normal group, the mean $FMF_{bone}$ angle is 78.1° (range 66.6-89.5°). FIGS. 2A and 2B show the $FMF_{bone}$ in chromosomally normal fetuses and trisomy 21 fetuses, respectively, as a function of crown-rump length. No significant association is found between the FMF angle, the fetal crown-rump length (r=0.058, p=0.318) and the nuchal translucency thickness (r=0.017, p=0.774). The median FMF angle is not significantly different between those euploid fetuses where the nasal bone is present or absent (mean difference 1.350, 95% CI=−2.310-5.010, p=0.469).

In the fetuses with trisomy 21, the mean $FMF_{bone}$ angle is 88.7° (range 75.4-104°). This is significantly larger than in the normal group (mean difference 10.60, 95% CI=9.5°-11.7°, p<0.001). Ninety eight percent of the trisomy 21 fetuses had an $FMF_{bone}$ angle, which is above the median angle (78.1°) of the normal group. Sixty nine percent of the trisomy 21 fetuses had $FMF_{bone}$ angles above the 95th percentile (85°) of the normal group and 40% of the trisomy 21 fetuses had $FMF_{bone}$ angles above the upper limit of the normal range (90°). There is no significant association between the $FMF_{bone}$ angle and crown-rump length (r=0.02, p=0.686) and nuchal translucency thickness (r=0.12, p=0.286). The median angle is not significantly different between those trisomy 21 fetuses with an absent or present nasal bone (mean difference 0.530, 95% CI=−1.860-2.940, p=0.658).

Mean percentage difference and the 95% limits of agreement between paired measurements of the $FMF_{bone}$ angle by the same sonographer in 30 cases and between paired measurements by different observers in 30 cases are shown in FIGS. 3A-3C and Table 1.

TABLE 1

Mean difference in percentage and the 95% limits of agreement between 30 paired measurements by the same sonographer and between 30 paired measurements by two sonographers

| Paired measurements | Mean difference (%) and SD | 95% Confidence interval |
| --- | --- | --- |
| Observer 1 | −0.004% (2.354) | −4.6 to 4.592 |
| Observer 2 | −0.008% (2.532) | −5.105 to 5.089 |
| Interobserver | 0.147 (2.673) | −5.021 to 5.315 |

Without intending to be limited by theory, the increased $FMF_{bone}$ angle in trisomy 21 fetuses noted in this study may be due to a dorsal displacement of the apex of the angle (i.e., the front of the maxilla) with respect to the forehead. This affect can also be produced by a certain degree of frontal bossing. However, frontal bossing is not recognized as a feature of trisomy 21. Lastly, the difference in the $FMF_{bone}$ angles could result from differences in the direction of the longitudinal axis of the upper palate—a deviation of this axis toward the base of the skull would lead to an increase in the FMF angle.

This study demonstrates the feasibility of measuring the $FMF_{bone}$ angle at 11-13$^{+6}$ weeks of gestation. The use of 3D ultrasound provides a perfect mid-sagittal view of the fetal face and rotation of the image to the optimal plane for measurement of the $FMF_{bone}$ angle. The maxilla is successfully visualized and the $FMF_{bone}$ angle is measured in all fetuses and in 95% of cases the difference between two consecutive measurements is less than 5°. This study further supports that feasibility of measuring the $FMF_{bone}$ angle in a fetus at from about 10 to about 40 weeks of gestation.

The potential utility in trisomy 21 detection is underscored by the fact that 69% of trisomy 21 fetuses have angle sizes which are above the 95th percentile of the normal range and the fact that 40% of the trisomy 21 fetuses have angle sizes that are above the upper limit of the normal range. It may also be useful in reducing the false positive rate—only 2% of the affected fetuses have angle sizes that are below the 50th percentile. Since the $FMF_{bone}$ angle is a continuous variable, likelihood ratios can be constructed for each measurement. The fact that there is no significant association between the $FMF_{bone}$ angle, nuchal translucency thickness, and the presence or absence of the nasal bone will allow its inclusion in the combined first trimester ultrasound-based assessment of risk for trisomy 21.

Example 2

This study involved a review of stored digital 2D images of fetal profiles, taken from singleton pregnancies before amniocentesis for fetal karyotyping at 14-24 weeks of gestation, wherein 100 consecutive pregnancies in which the fetal karyotype was normal and 34 fetuses with trisomy 21 were examined. All images were obtained using Sequoia 512 (Siemens) system. The angles were measured using on-line tools in the KinetDx (Siemens) PAC system.

The following data were retrieved from the patient records: maternal age, gestational age, indication for karyotyping, the findings at the ultrasound examination carried out before amniocentesis, including fetal abnormalities or markers for aneuploidy and presence or absence of the nasal bone.

Figure 4B:
Figure 4A:
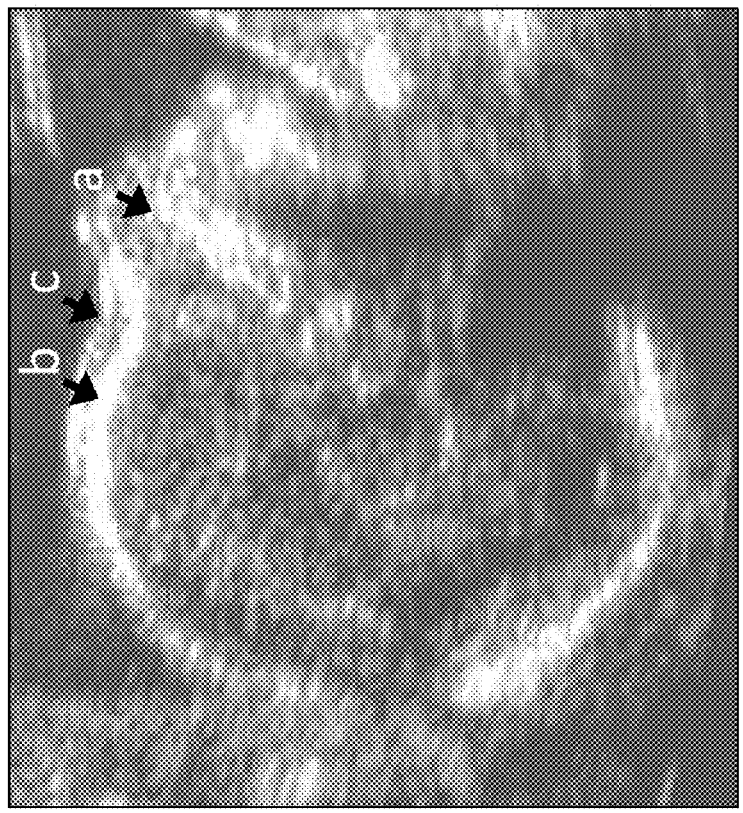

The images had been obtained by transabdominal sonography with the fetus facing the transducer. The ideal angle of insonation with respect to the longitudinal axis of the upper palate was determined to be about 45°. In this plane the upper palate approximates the shape of a rectangle as shown in FIG. 4A. The upper and lower edges of the upper palate were seen as two parallel lines, which were most clearly visible in the front half of the upper palate as the posterior half usually had a thickened and irregular appearance. Occasionally, a hyperechoic line coursing diagonally thorough the upper palate could be seen and caution was taken to avoid mistaking this line as the upper border of the palate, as shown in FIG. 4B.

Figure 5B:
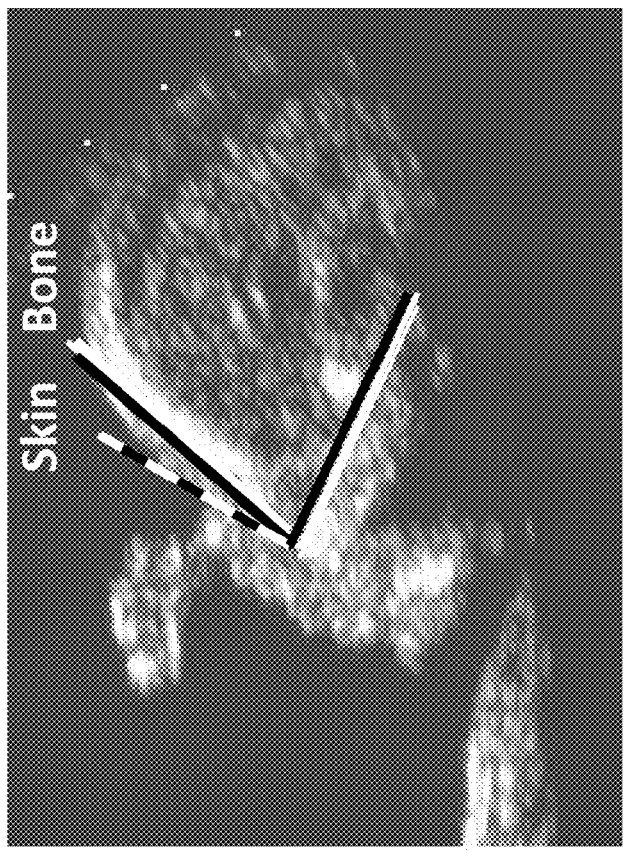
FIGS. 5A and 5B show fronto-maxillary facial angles to bone ($FMF_{bone}$) and to skin ($FMF_{skin}$) in a euploid fetus and a fetus with trisomy 21, respectively.
Figure 5A:
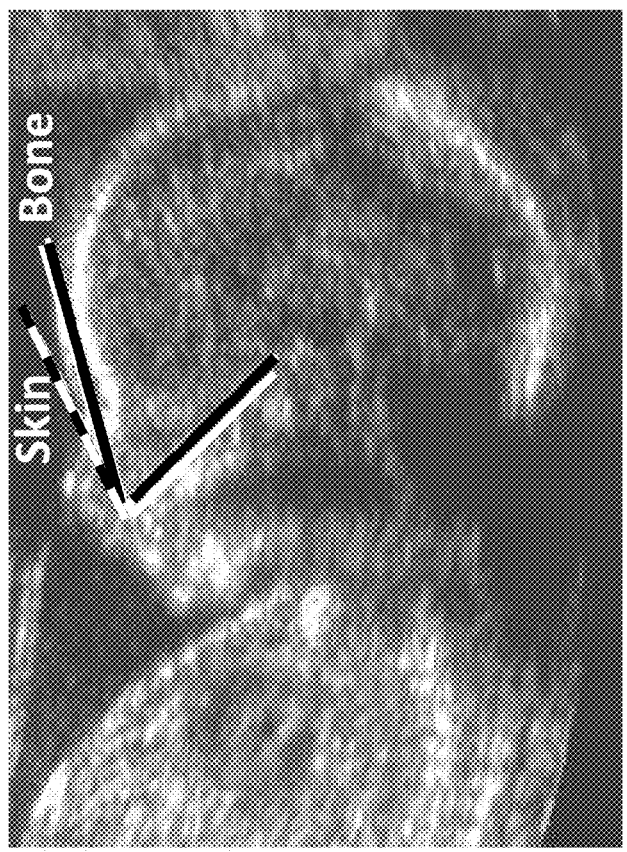

The angle between the top edge of the upper palate and the boney forehead ($FMF_{bone}$) and between the top edge of the upper palate and the skin over the forehead ($FMF_{skin}$) as shown in FIGS. 5A and 5B, respectively, was measured. Both angle measurements were attempted in each fetus. First, a ray of the FMF angle was drawn along the upper line seen in the front half of the upper palate as shown in FIGS. 4A, 5A and 5B. Second, the vertex of the angle was defined as the forward-most portion of the maxilla where it is intersected by the upper line (FIGS. 5A and 5B). Third, the second ray of the angle was drawn from the vertex to either the front part of the boney forehead ($FMF_{bone}$) or to the external surface of the skin over the lower part of the forehead just before the skin begins its anterior course over the nasal bridge ($FMF_{skin}$). All images where a good fetal profile was obtained and a line along the upper the edge of the upper palate could be generated were used.

One investigator initiated the technique for FMF angle measurements and applied it to the 134 fetuses, whilst knowing the karyotype. He subsequently repeated the measurements without knowledge of the results obtained on the first occasion. Another investigator received instructions and training in the technique. She then independently performed FMF angle measurements in the same fetuses without knowing the karyotype.

In the chromosomally normal group, regression analysis was used to determine the significance of the association between each of the two FMF angles and gestational age. The measured angles in each euploid and trisomy 21 fetus were then expressed as a difference from the appropriate expected mean for gestation (delta value), the Kolmogorov-Smirnov test was used to determine if the samples were normally distributed, and Student t-test was used to determine the significance of difference in the delta values between the euploid and trisomy 21 fetuses.

The likelihood ratios for trisomy 21 were calculated for different cut-offs in the delta values of $FMF_{bone}$ and $FMF_{skin}$.

The Mann-Whitney U test was used to determine the significance of difference in the delta values between the trisomy 21 fetuses with and with absent nasal bone.

The Bland-Altman analysis was used to compare the measurement agreement and bias for a single examiner and between two examiners. The data were analyzed using the statistical software SPSS 12 (Chicago, Ill., USA), and a p value of less than 0.05 was considered statistically significant.

The median maternal age in the euploid group was not significantly different from that in the trisomy 21 fetuses (median 33.1 years, range 15-45 vs. 34.2 years, range 21-44; 95% CI −4.12 to 1.23, p=0.29). Similarly, there were no significant differences between the groups in gestational age (median 18.0 weeks, range 14.4-23.9 vs. median 18.7 weeks, range 14.1-22.3; 95% CI −1.47 to 0.26, p=0.17). The indications for amniocentesis in the 134 cases were advanced maternal age or anxiety (n=76), abnormal second trimester serum screen (n=54), previous child or fetus with trisomy 21 (n=2), maternal balanced translocation (n=1), and fetal abnormalities detected by ultrasound (n=46). The ultrasound findings before amniocentesis in both populations are summarized in Table 2.

TABLE 2

Ultrasound findings in fetuses before amniocentesis.

| Indication for amniocentesis | Normal karyotype | trisomy 21 |
|---|---|---|
| Absent nasal bone | 2 (2%) | 19 (55.9%) |
| Cardiac defect | 2 (2%) | 6 (17.6%) |
| Thickened nuchal fold | — | 8 (23.5%) |
| Pleural effusion | — | 2 (5.9%) |
| Mild ventriculomegaly | 1 (1%) | 1 (2.9%) |
| Echogenic bowel | — | 1 (2.9%) |
| Omphalocele | 1 (1%) | 1 (2.9%) |
| Clubbed feet | — | 1 (2.9%) |
| Small/large stomach | — | 1 (2.9%) |

The quality of the stored images was sufficiently good to allow the measurement of at least one of the two FMF angles in all 134 cases. In the euploid group, the FMF angles decreased linearly with gestation (Table 3). In the trisomy 21 fetuses, the FMF angles were significantly wider than in the euploid group (Table 4, FIG. 6).

TABLE 3

Relation between the two fronto-maxillary facial (FMF) angle measurements and gestational age in the euploid fetuses.

| FMF angle | N | Change with gestation | SD | r | p |
|---|---|---|---|---|---|
| FMF Bone | 100 | 86.2-1.005 × gestational weeks | 5.30 | 0.371 | <0.0001 |
| FMF Skin | 94 | 87.8-0.665 × gestational weeks | 5.95 | 0.232 | 0.025 |

TABLE 4

Comparison of the two fronto-maxillary facial (FMF) angle measurements between the euploid and trisomy 21 fetuses.

| FMF angle | n | Mean difference (95% CI) | p | Above 95th percentile |
|---|---|---|---|---|
| FMF Bone | 34 | 10.78 (8.40-13.20) | <0.0001 | 27 (79.4%) |
| FMF Skin | 33 | 16.82 (14.0-19.70) | <0.0001 | 29 (87.9%) |

The likelihood ratios for trisomy 21 for different cut-offs in the delta values of $FMF_{bone}$ and $FMF_{skin}$ are shown in Table 5.

TABLE 5

Positive and negative likelihood ratios for trisomy 21 were calculated for different cut-offs in the delta values of the two fronto-maxillary facial (FMF) angles. The delta value is the difference in degrees in a measured FMF angle from the appropriate normal mean for gestation.

| | Fronto-maxillary facial angle to bone | | | | Fronto-maxillary facial angle to skin | | | |
|---|---|---|---|---|---|---|---|---|
| Cut-off (Delta value°) | Normal N = 100 | Trisomy 21 N = 34 | LR + ve | LR − ve | Normal N = 94 | Trisomy 21 N = 33 | LR + ve | LR − ve |
| ≧12 | 1 (1%) | 12 (35.3%) | 35.3 | 0.65 | 2 (2.1%) | 27 (81.8%) | 38.9 | 0.19 |
| ≧10 | 2 (2%) | 16 (47.1%) | 23.6 | 0.54 | 3 (3.2%) | 29 (87.8%) | 27.4 | 0.13 |
| ≧8 | 7 (7%) | 21 (61.8%) | 8.8 | 0.41 | 8 (8.5%) | 29 (87.8%) | 10.3 | 0.13 |
| ≧6 | 15 (15%) | 29 (85.3%) | 5.7 | 0.17 | 16 (17.0%) | 31 (93.9%) | 5.5 | 0.07 |
| ≧4 | 23 (23%) | 31 (91.2%) | 4.0 | 0.11 | 22 (23.4%) | 32 (96.9%) | 4.1 | 0.04 |
| ≧2 | 35 (35%) | 32 (94.1%) | 2.7 | 0.09 | 33 (35.1%) | 33 (100%) | 0.35 | — |
| ≧0 | 50 (50%) | 33 (97.1%) | 1.9 | 0.06 | 51 (54.3%) | 33 (100%) | 0.54 | — |

LR = likelihood ratio

The nasal bone was recorded as being absent in 19 (55.9%) and present in 15 (44.1%) of the 34 trisomy 21 fetuses. There was no significant difference between the two groups in either of the two FMF angles (Table 6). In the chromosomally normal fetuses only two (2%) had an absent nasal bone.

TABLE 6

Comparison of the two fronto-maxillary facial (FMF) angle measurements between trisomy 21 with and with absent nasal bone.

| FMF angle | Nasal bone present | | Nasal bone absent | | |
|---|---|---|---|---|---|
| | n | Mean difference (95% CI) | n | Mean Difference (95% CI) | p |
| FMF Bone | 15 | 11.5 (6.65-16.36) | 19 | 10.22 (8.57-11.57) | 0.876 |
| FMF Skin | 14 | 17.2 (11.63-22.76) | 19 | 16.55 (14-19.1) | 0.942 |

In the measurement of $FMF_{bone}$, the mean difference, with 95% limits of agreement, between paired measurements by the same sonographer was −0.40 (−8.1 to 7.3) % and between paired measurements by two sonographers was 0.66 (−8.6 to 9.8) %. The respective values for $FMF_{skin}$, were −0.77 (−8.3 to 6.8) % and 0.84 (−10.3 to 9.37) %.

The data of this retrospective study suggest that sonographic measurement of FMF angles during the second trimester of pregnancy is likely to prove useful in prenatal screening for trisomy 21. For a false positive rate of 5%, the use of the FMF angle can detect more than 85% of fetuses with trisomy 21. A large FMF angle may be the single most sensitive second-trimester marker of trisomy 21. In screening for trisomy 21 by maternal age alone or maternal age and second-trimester maternal serum biochemistry, the detection rates, for a false positive rate of 5%, are 30% and 65%, respectively.

The FMF angle is a continuous variable, unlike other measurements used for screening in the second trimester. As such, likelihood ratios can be generated for each angle measurement. In euploid fetuses, both FMF angles decrease with gestation and consequently gestation should be taken into account in deciding whether in a given patient an angle measurement would be associated with an increase or decrease in the a priori risk for trisomy 21.

The detection rate of trisomy 21 was about 10% higher with the $FMF_{skin}$ than the $FMF_{bone}$. In second trimester fetuses with trisomy 21, there is skin edema both in the neck and in the prenasal region. Consequently, the new marker $FMF_{skin}$ combines two distinguishing features of trisomy 21, namely dorsal displacement of the maxilla and increase in skin thickness.

An additional finding of this study is that in trisomy 21 fetuses the FMF angles appear to be independent of the presence or absence of nasal bone hypoplasia. Consequently, the two sonographic markers, which are in any case observed in the same fetal profile view, could be combined for an even higher detection rate of affected fetuses.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A method for prenatal screening for trisomy 21 using an ultrasound imaging system comprising an ultrasound device and a computing device, the method comprising: obtaining a two or three dimensional image of a fetal face using the ultrasound device, measuring a $FMF_{bone}$ angle on the image using the computing device, wherein the $FMF_{bone}$ angle is the angle between a line extending along an upper aspect of a maxilla and a line extending from an anterior aspect of the maxilla to an external surface of a frontal bone at its point of greatest anterior excursion (the $FMF_{bone}$ angle), and comparing the measured $FMF_{bone}$ angle with an $FMF_{bone}$ angle characteristic of chromosomally normal fetuses using the computing device to provide an indication of an occurrence of trisomy 21 in a fetus, wherein a measured $FMF_{bone}$ angle greater than the $FMF_{bone}$ angle characteristic of chromosomally normal fetuses provides an indication of an increased likelihood of the occurrence of trisomy 21 in the fetus.

2. The method of claim 1, wherein the ultrasound device is a three dimensional ultrasound device.

3. The method of claim 2, wherein the image comprises a mid-sagittal view of the fetal face.

4. The method of claim 1, wherein the image is obtained from a fetus at 10 or greater weeks of gestation.

5. The method of claim 1, wherein the image is obtained from a fetus at 10-19 weeks of gestation.

6. The method of claim 1, wherein the image is obtained from a fetus at 10-13 weeks of gestation.

7. The method of claim 1, wherein the image is obtained from a fetus at 14-23 weeks of gestation.

8. The method of claim 1, wherein a measured $FMF_{bone}$ angle of greater than 80° indicates an increased likelihood of the occurrence of trisomy 21.

9. The method of claim 1, wherein a measured $FMF_{bone}$ angle of greater than 90° indicates an increased likelihood of the occurrence of trisomy 21.

10. The method of claim 1, wherein the $FMF_{bone}$ angle is the angle between a line extending along an upper aspect of a maxilla and a vomer bone and a line extending from an anterior aspect of the maxilla to an external surface of a frontal bone at its point of greatest anterior excursion.

11. A method for prenatal screening for trisomy 21 in a fetus at 14-23 weeks of gestation using an ultrasound imaging system comprising an ultrasound device and a computing device, the method comprising: obtaining a two or three dimensional image of a fetal face using the ultrasound device, measuring a $FMF_{skin}$ angle on the image using the computing device, wherein the $FMF_{skin}$ angle is the angle between a line extending along an upper aspect of a maxilla and a line extending from an anterior aspect of the maxilla to an external skin surface along a frontal bone at its point of greatest anterior excursion (the $FMF_{skin}$ angle), and comparing the measured $FMF_{skin}$ angle with an $FMF_{skin}$ angle characteristic of chromosomally normal fetuses using the computing device to provide an indication of an occurrence of trisomy 21 in a fetus, wherein a measured $FMF_{skin}$ angle greater than the $FMF_{skin}$ angle characteristic of chromosomally normal fetuses provides an indication of a likelihood of the occurrence of trisomy 21 in the fetus.

12. The method of claim 11, wherein the ultrasound device is a three dimensional ultrasound device.

13. The method of claim 12, wherein the image comprises a mid-sagittal view of the fetal face.

14. The method of claim 11, wherein a measured $FMF_{skin}$ angle of greater than 80° indicates an increased likelihood of the occurrence of trisomy 21.

15. The method of claim 11, wherein a measured $FMF_{skin}$ angle of greater than 85° indicates an increased likelihood of the occurrence of trisomy 21.

16. The method of claim 11, wherein the $FMF_{skin}$ angle is the angle between a line extending along an upper aspect of a maxilla and a vomer bone and a line extending from an anterior aspect of the maxilla to an external skin surface along a frontal bone at its point of greatest anterior excursion.

17. The method of claim 11, further comprising measuring a $FMF_{bone}$ angle on the image using a computing device, wherein the $FMF_{bone}$ angle is the angle between a line extending along the upper aspect of the maxilla and a line extending from the anterior aspect of the maxilla to an external surface of a frontal bone at its point of greatest anterior excursion (the $FMF_{bone}$ angle), and comparing the measured $FMF_{bone}$ angle with an $FMF_{bone}$ angle characteristic of chromosomally normal fetuses using a computing device to provide an indication of an occurrence of trisomy 21 in a fetus, wherein a measured $FMF_{bone}$ angle greater than the $FMF_{bone}$ angle characteristic of chromosomally normal fetuses provides an indication of an increased likelihood of the occurrence of trisomy 21 in the fetus.

18. The method of claim 17, wherein the $FMF_{bone}$ angle is measured from an image obtained from the fetus at 10-13 weeks of gestation.

19. The method of claim 18, wherein the ultrasound device is a three dimensional ultrasound device.

* * * * *